United States Patent [19]

Somlyai

[11] Patent Number: 5,855,921
[45] Date of Patent: Jan. 5, 1999

[54] PHARMACEUTICAL PRODUCTS FOR CURING TUMOROUS DISEASES AND PROCESS FOR PREPARING SAME

[76] Inventor: Gábor Somlyai, 51/a, Deák F. u., Budapest 1215, Hungary

[21] Appl. No.: 211,941

[22] PCT Filed: Sep. 28, 1992

[86] PCT No.: PCT/HU92/00036

§ 371 Date: Jun. 2, 1994

§ 102(e) Date: Jun. 2, 1994

[87] PCT Pub. No.: WO93/08794

PCT Pub. Date: May 13, 1993

[30] Foreign Application Priority Data

Oct. 31, 1991 [HU] Hungary ................................ 3437/91

[51] Int. Cl.⁶ ........................................... A61K 9/08
[52] U.S. Cl. ................... 424/600; 423/580.2; 423/647.7
[58] Field of Search .................. 424/600; 423/580.2, 423/647.7

[56] References Cited

U.S. PATENT DOCUMENTS

| | | | |
|---|---|---|---|
| 3,807,960 | 4/1974 | Thayer | 23/270 R |
| 4,411,798 | 10/1983 | Chan | 210/727 |
| 4,444,737 | 4/1984 | Tsuchiya et al. | 423/249 |
| 5,223,269 | 6/1993 | Liepins | 424/600 |

OTHER PUBLICATIONS

The Merck Index, 10th Ed (1983) pp. 424–425.

Remingtons Pharmaceutical Sciences, 16th Ed., Arthur Osol, Editor in Chief (Jan. 1980) pp. 1239–1243.

Internal Medicine, 4th Ed. Editor–in–Chief Jay Stein, pp. 699–715 (Jan. 1993).

*Primary Examiner*—Brian M. Burn
*Attorney, Agent, or Firm*—Gordon-Lendvay & Catan

[57] ABSTRACT

The invention relates to products for curing tumorous diseases, comprising as active agent water or aqueous solutons, suitable for human consumption, having a deuterium content of 0.1 to 110 ppm, optionally together with carriers and/or auxilliaries, in the form of pharmaceutical products or medicinal solutions. Furthermore, the invention relates to a process for preparing these products.

34 Claims, 2 Drawing Sheets

PHARMACEUTICAL PRODUCTS FOR CURING TUMOROUS DISEASES AND PROCESS FOR PREPARING SAME

This invention relates to pharmaceutical products for curing tumorous diseases and a process or preparing same.

Nowadays there are a number of methods (surgical intervention, therapy by irradiation, hormonotherapy, applying antitumor agents) for combatting against malignant tumors. All these methods together with the recent results in diagnostics have resulted in major advances in the last decade, but in spite of these results the applied methods have many disadvantages.

The main reason of the problem is that since the molecular mechanism of the cell-proliferation is still not known, the intervention into the course of the disease by the available means is rather difficult. It is therefore that the way of the recovery or at least a delay in the development of the disease involve frequently the removal of some parts of organs or troubles in the blood-forming process when antitumor agents, etc. are used.

The proper answer to this question can be expected only with full knowledge of the (sub) molecular processes playing a key role in initiating the cell proliferation.

By means of the development of the molecular biology, biological science is just before recognizing the decisive regulating processes through which it will be possible to restore patients suffering from tumorous diseases to health.

Taking into consideration the recent results of molecular biology the conclusion can be drawn that a common early response of eukaryotic cells to stimuli which activate the proliferation is an increase in intracellular pH due to an exchange of extracellular $Na^+$ for intracellular $H^+$ across the plasma membrane [P.N.A.S. 79, 7778–7782 (1982)]. The conclusion that the activation of the $Na^+/H^+$ exchange system is indispensable to initiate the cell growth has been supported by numerous experimental results.

It was found that specific mutation abolishing $Na^+/H^+$ exchange system precluded growth of cells at neutral and acidic pH [P.N.A.S. 81, 4833–4837 (1984)].

Recent evidence suggests that growth factors activate $Na^+/H^+$ exchange system suggesting that $Na^+/H^+$ exchange may function as a transmembrane signal transducer [Nature 304, 645–648 (1983)].

The relationship between the activated $Na^+/H^+$ exchange system and the tumorous character of cell lines have been proved, too. The pH was found to be increased after transformation of cell line comparing to the nontumorigenic parental line [(P.N.A.S. 84, 2766–2770 (1987)]. Strong correlation was found between the expression of oncogene and the elevated intracellular pH, because injecting the protein encoded by Ha-ras or the expression of V-mos and Ha-ras oncogenes in the cell increased the intracellular pH by activating the $Na^+/H^+$ exchange system [Mol. Cell. Biol. 7, 1984–1988 (1987); Gene 54, 147–153 (1987)].

Similar changes were found by activating another membrane-bound hydrogen-ion transport system. In this case an ATPase gene was isolated from yeast, and used to transform mouse and monkey cell lines. The gene was expressed and the ATPase, by continually extruding protons, caused a sustained alkalinization of the cytoplasm. The really surprising result of this experiment was that the cells transformed by the gene of ATPase of the yeast acquired tumorigenic properties [Nature 334, 438–440 (1988)].

This latest experiment proves that the induction of cell proliferation is connected not only with the activation of the $Na^+/H^+$ exchange system, but also with the activation of an other proton-extruding system which can serve as a signal to cell proliferation, in general.

A simple explanation for the above phenomenon can be that the cell proliferation is initiated by increase in intracellular pH. This explanation was, however, not confirmed by the experiments in which an artificial increase in cytoplasmic pH has not raised the cell proliferation activity [J. Exp. Biol. 124, 359–373 (1986)].

The above-mentioned molecular processes can be interpreted by investigating the possible role of hydrogen and of deuterium in controlling the above processes.

In nature the ratio of hydrogen to deuterium is about 6000:1. Because of the mass difference of 100% the two isotopes show different behaviour in chemical reactions. It is a generally accepted view that the D-bonds participating in chemical reactions can be split at a lower rate because of the isotope effect, therefore they need an augmented activation energy [Simonyi Miklós and Fitos Ilona: Hydrogen Isotope Effect in Chemical Reactions. A kémia újabb eredményei (in Hungarian). (Recent Results in Chemistry) 46, 8–129 (1980)]. In enzymatic reactions it can be similarly measured that the reaction rate is of from 4 to 5 times higher with the hydrogen isotope having the smaller mass number [Biochem. Pharmacol. 30, 3089–3094 (1981)].

The effects of the deuterium have been thoroughly investigated in biological systems, too [Katz, J. J. and Crespi, H. L.: Isotope Effects in Biological Systems (eds. Collins, C. J. and Bowman, N. S.) A.C.S. Monograph 167, van Nostrand Reinhold, New York, 1971, 286–363]. The common characteristic of these experiments is that the investigation of the deuterium effects is usually carried out by applying high (1–100%) $D_2O$ concentrations.

It is widely accepted that the deuterium has an inhibiting activity to the reproduction and growth of bacteria, yeasts and plants. Mammalia can tolerate the $D_2O$ in a concentration of at most 35%; a higher concentration of $D_2O$ has a lethal effect to them.

In these experiments the deuterium was applied in from 100 to 10,000 times higher concentrations than the natural concentration which was ignored.

A world-wide survey of hydrogen isotopes in precipitations revealed that the D content covers a range of 120–160 ppm depending mainly on the site of sampling. Plants and thus also algae differentiating between hydrogen isotopes are able to enrich hydrogen [Schiegl, W. E. and Vogel, J. C., Earth and Planet. Sci. Letters 7, 307–313 (1970); Ziegler, H. et al., Planta 128, 85–92 (1976)]. As a result of these processes the deuterium concentrations e. g. in plant-eating creatures show alterations in a narrow range, depending on the species and quantities of the plants consumed. In case of humans the area, where the consumed plants were cultivated, is a decisive factor. According to measurements the deuterium content of the rainfall on the tropics is 155–160 ppm, whereas this value is only 120–150 ppm in the temperate zones of the world. The difference becomes visible in the deuterium content of the plants, too, with alterations of up to 10–20 %.

Though the above-mentioned phenomena have been observed, the experts have not attached any importance to the deuterium content in biological systems.

The aim to be achieved by the invention was to develop pharmaceutical products suitable for preventing cancer or inhibiting the tumor growth and, in this way, curing cancer diseases.

The basis of the invention is the recognition that the deuterium content of very low level (120–160 ppm) in biological systems is essential for maintaining the normal rate of cell proliferation and the deficiency of deuterium increases the length of cell cycles. It was namely realized that the deuterium is a component of a submolecular regulating system and the processes temporarily elevating the concentration of D trigger cell proliferation.

A further basis of the invention is the recognition that by applying water or aqueous solutions containing deuterium in an amount less than the deuterium content of natural waters (e.g. juices diluted with deuterium-depleted water), the deuterium level in the human organism can be decreased as a result of exchange processes and in this way the proliferation of tumorigenic cells can be stopped or the development of cancerous tumors can be prevented.

Consequently, the invention relates to products for curing tumorous diseases, comprising water with a deuterium content of 0.1 to 110 ppm and/or aqueous solutions, suitable for human consumption, with a deuterium content of 0.1 to 110 ppm as active agent, optionally together with carriers and/or auxiliaries.

The products according to the invention are preferably pharmaceutical products like physiological salt solutions, or medicinal solutions like fruit syrups, soft drinks, or beer with reduced alcohol content or free from alcohol, having a deuterium content of 0.1 to 110 ppm.

Furthermore, the invention relates to a process for preparing products for curing tumorous diseases, comprising the steps of producing by electrolysis and/or distillation water and/or aqueous solutions having a deuterium content of 0.1 to 110 ppm as the active agent, then transforming the thus-produced water and/or aqueous solution having a deuterium content of 0.1 to 110 ppm optionally together with carriers and auxiliaries to pharmaceutical products or medicinal solutions.

According to a preferred method of execution of the claimed process physiological salt solutions are prepared as pharmaceutical products having a deuterium content of 0.1 to 110 ppm.

According to a further preferable method of execution of the process of the invention fruit syrups, soft drinks, or beer with no or reduced alcohol content are prepared as medicinal solutions having a deuterium content of 0.1 to 110 ppm.

The products according to the invention are preferably formulated as injectable solutions, infusion solutions, syrups, juices or hydrating ointments having a deuterium content of 0.1 to 110 ppm.

The products according to the invention are suitable for curing tumorous diseases. The basis of this therapeutical application is the fact that by applying deuterium-depleted solutions containing deuterium from 0.1 to 110 ppm the deuterium level of the organism decreases, too. In consequence of this process the growth rate of the tumorous cells is slowing, then these cells will decay, while the healthy cells are still capable of tolerating decreasing deuterium concentration.

The suitability of the process according to the invention for treating tumourous diseases has been proved by in vitro and in vivo tests carried out by using deuterium-depleted water. The test results can be seen in FIGS. 1 and 2 as well as in Tables 1 to 4.

When the hydrogen obtained by electrolyzing water was burned to water according to Example 1, water containing deuterium in an amount of 30–40 ppm was produced. Water containing deuterium in higher concentrations than natural waters was prepared by adding $D_2O$ of 99,78% by mass to normal water. Culture media suitable for maintaining in vitro different animal cell lines were produced of the so-prepared waters having different deuterium contents by dissolving 10 g of a commercially-produced dehydrated mixture of amino acids, vitamins, salts and bases [Dulbecco's modified Eagle's medium (D'MEM), code number: 074-01600; Sigma, St. Louis, USA] in 1 litre of water. 110 ml of bovine serum were added to the so-prepared solutions. The so-obtained liquid medium contained all the compounds needed for maintaining cells.

The growth of mouse-fibroblast cells $L_{929}$ was first studied under in vitro conditions in nutrient media containing deuterium in different amounts (30–5000 ppm). By these experiments the division of about 400 individual cells was followed. The experiments proved that the cell growth rate in a medium prepared with D-depleted water was reduced by 15–20%.

Figure 1:
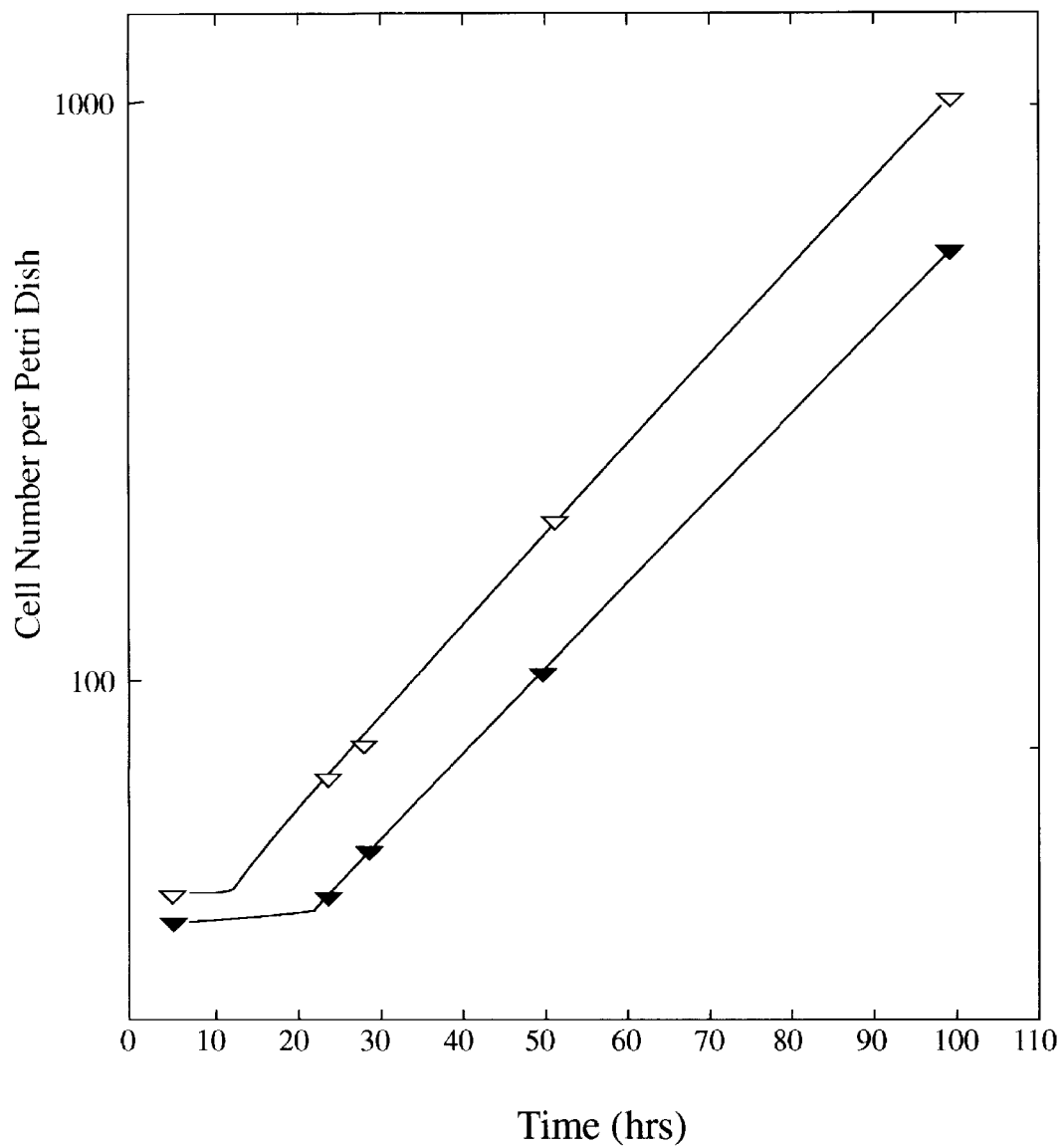
In FIG. 1 the growth of mouse-fibroblast cells $L_{929}$ is illustrated after synchronization in phase G1 in nutrient fluids prepared by using water having decreased (v: 30 ppm) or normal (v: 150) deuterium content.

Then it was investigated whether the deuterium concentration of the nutrient media influenced the length of time necessary for the cell to enter into S-phase from the so-called G1 phase after synchronization (FIG. 1). It can be seen in FIG. 1 that, after synchronizing, the growth of the cells started 6–8 hours later and the growth rate was lower in nutrient media prepared with D-depleted water (v: 30 ppm) than in water of normal deuterium level (v: 150 ppm).

Figure 2:
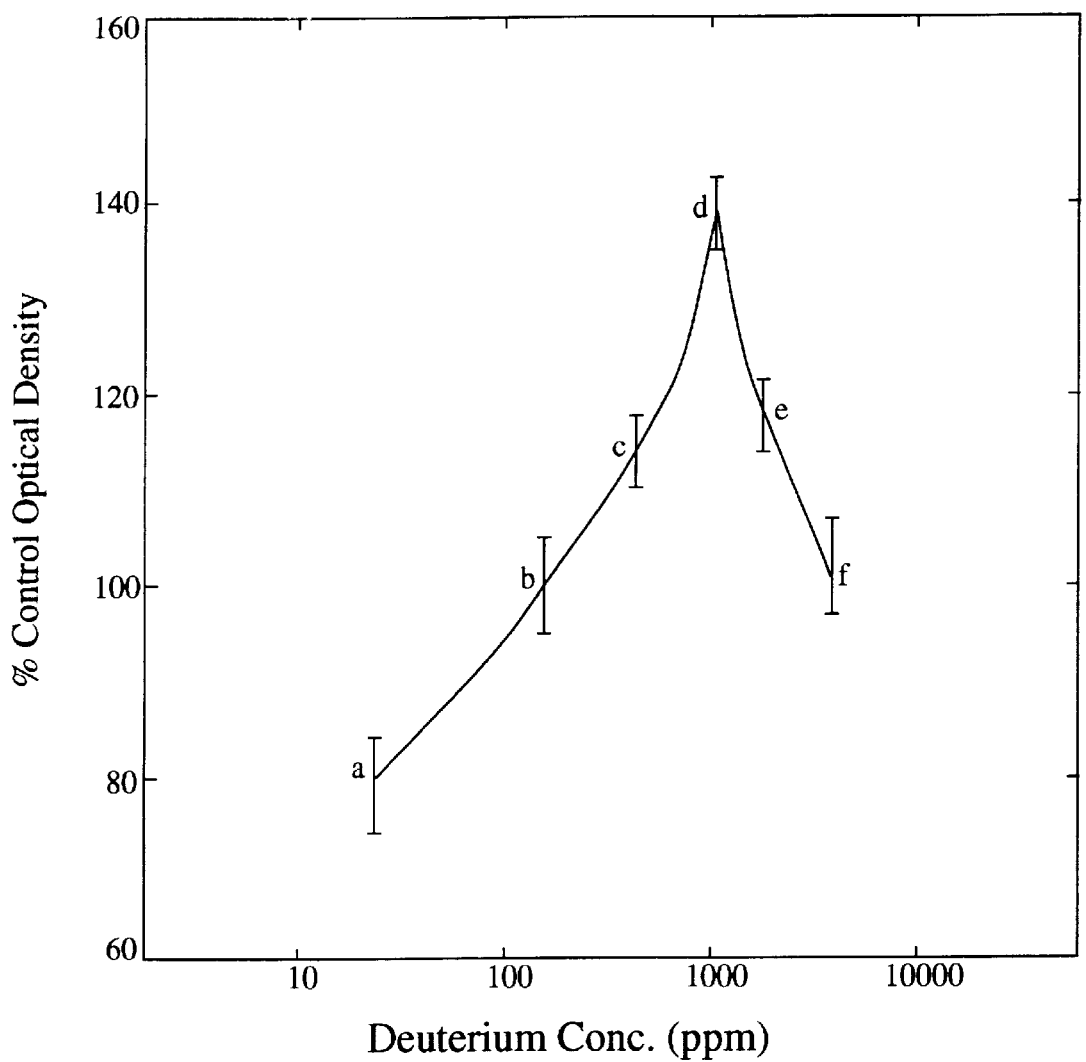
In FIG. 2 the results obtained at determining the relative amount of mouse-fibroblast cells $L_{929}$ is illustrated after cultivating them in nutrient fluid media containing deuterium in an amount of 30 to 5000 ppm (a: 30; b: 150; c: 300; d: 600; e: 1250; f: 5000 ppm D).

A method generally accepted in the recent years for determining the number of cells is carried out by incubating the cells together with 2,3-bis(2-methoxy-4-nitro-5-sulfophenyl)-5-[(phenylamino)carbonyl]-2H-tetrazolium-hydroxide (XTT) which compound is reduced by the cells. The reduced form of this compound shows an absorption maximum at 450 nm and thereby its amount can be photometrically measured; thus, the relative cell number can be calculated from the optical density (OD) values [Cancer Research 48, 4827–4833 (1988)]. By this method the effects of deuterium concentrations lower (30 ppm) and higher (300–5000 ppm) than the natural level on cell proliferation were also studied (FIG. 2). It was proved by the experiments that the growth rate was slowing down in nutrient media prepared with deuterium-depleted water. According to these experiments deuterium concentrations from 2 to 4 times higher than the natural one (300 and 600 ppm) exert a stimulating effect on cell-proliferation. [Increasing further the deuterium concentration (1250 and 5000 ppm) the inhibition deriving from the isotope effect will become dominant.] Having repeated the tests with four further different cell lines similar results were obtained.

In the first in vivo experiment it was investigated how the growth of the tumors was influenced by decreasing the deuterium content in the drinking water of mice. Human breast tumours MDA-MB-231 and MCF-7 were transplanted into two groups of 14 CBA/Ca mice each. The animals of the control group consumed normal water, while from the day following the transplantation the animals belonging to the treated groups were supplied with D-depleted water prepared according to the invention. The results are summarized in Table 1.

TABLE 1

Effect of deuterium-depleted water on the growth of breast tumour in mice

| Cell line | MDA-MB-231 | | MCF-7 | |
|---|---|---|---|---|
| Days | Control | Treated | Control | Treated |
| 20 | 5/5 | 9/9 | 6/6 | 8/8 |
| 50 | 5/5 | 5/9 | 6/6 | 5/8 |
| 65 | 1/1 | 4/8 | 2/2 | 4/7 |
| 71 | 0/0 | 3/8 | 1/2 | 2/7 |
| 80 | 0/0 | 2/7 | 0/1 | 0/5 |
| 87 | 0/0 | 1/6 | 0/1 | 0/5 |

The numbers in the treated and control groups correspond to the numbers of tumorous/all animals.

The results in Table 1 show that spontaneous tumour regression could be experienced only in one animal of the 11 tumourous animals in the two control groups (5+6), the others perished on the 71th and 80th day, resp., after transplantation. In the two treated groups, on the contrary, the tumor, after having grown, regressed and then disappeared in 10 animals (59%) of the 17 tumorous animals (9+8) and one of the tumorous animals, which is not shown in Table 1, survived by 30 days the animal which died at the latest in the control group. These animals got drinking water containing 30 ppm of deuterium for 3 weeks, then water containing 110–120 ppm of deuterium to the end of the experiment.

Carrying out an other experiment tumorous human prostatic cells PC-3 were transplanted into mice of 44 CBA/Ca type. The treatment started on the 32nd day after transplantation by giving the animals water containing 94±5 ppm of deuterium to drink. At this time the average tumour diameter was 10.4 mm and 10.2 mm in the control and the treated groups, respectively. (Taking into consideration the body/tumour mass ratio, the treatment of the mice at this stage of the experiments corresponds to starting the cure of a human being of 70 kg body mass with a tumour of 3,5 kg.) Thus, the treatment was started in a very advanced stage of tumor, and that was the reason why the treatment was not as effective as in the first experiment. The numbers in Table 2 represent the number of the tumorous/all animals and the average tumor size changing in the of the treatment.

TABLE 2

Effect of deuterium-depleted water on PC-3 prostatic tumor in mice

| | Tumorous/all animals | | Average tumour diameter (mm) | |
|---|---|---|---|---|
| Days | Control | Treated | Control | Treated |
| 32 | 22/22 | 22/22 | 10.4 | 10.2 |
| 39 | 17/17 | 19/20 | 14.6 | 11.1 |
| 46 | 13/13 | 17/19 | 22.4 | 17.5 |
| 53 | 9/9 | 11/14 | 21.7 | 15.0 |
| 60 | 6/7 | 10/13 | 23.8 | 15.0 |
| 67 | 3/4 | 10/13 | 16.7 | 18.0 |
| 74 | 3/4 | 7/10 | 24.0 | 18.1 |
| 81 | 3/4 | 5/8 | 28.6 | 18.0 |
| 88 | 2/3 | 5/8 | 37.0 | 16.6 |

The results in Table 2 show that in the control group only 3 animals (13%) out of 22 survived the 87th day after transplantation of the tumorous cells, while in the treated group 8 animals (36%) out of 22 were still alive on the 88th day. At this time two animals (9%) and five animals (23%), resp., were alive in the control and the treated groups, respectively. In 3 animals of the treated group tumor regression could be observed. A significant difference between the treated and the control groups, resp., is confirmed by the data of the average tumor diameter, too.

On the basis of the data in Table 2 cumulative mortality data are summarized in Table 3.

TABLE 3

Cumulative mortality data on PC-3 prostatic tumor

| Days | Control | Treated |
|---|---|---|
| 32 | 0 | 0 |
| 39 | 5 | 2 |
| 46 | 9 | 3 |
| 53 | 13 | 8 |
| 60 | 15 | 9 |
| 67 | 18 | 9 |
| 74 | 18 | 12 |
| 81 | 18 | 14 |
| 88 | 19 | 14 |

The results in Table 3 show that the number of animals perished in the treated group was smaller than that of the control group in all stages of the test. It is worth accentuating that by the 67th day after transplantation only 9 animals perished in the treated group, while twice as much animals (18) perished in the control group. The importance of this difference is underlined by the fact that the tumor development period of one week in mice corresponds to a period of 200–300 days in humans. Thus the data in Table 3 show that the survival period of humans can be increased by years, even if the medical cure starts in an advanced stage of the disease.

In a third experiment tumourous HT-29 colon cells were transplanted into mice. The treatment by giving the animals water containing 94±5 ppm of deuterium to drink started on the 24th day after transplantation. The average tumor volumes can be seen in Table 4. The control group consisted of 13 animals and the treated group of 16 animals. It appears from Table 4 that during the 90-day treating period the average tumor volumes were considerably lower in the treated group than in the control group.

TABLE 4

Effect of D-depleted water on tumourous human HT-29 colon cells in mice

| | Average of tumor volumes, cm$^3$ | |
|---|---|---|
| Days | Control | Treated |
| 1 | 0.16 | 0.16 |
| 20 | 0.81 | 0.45 |
| 35 | 2.28 | 1.88 |
| 55 | 5.82 | 4.85 |
| 70 | 8.09 | 6.80 |
| 85 | 19.48 | 10.96 |
| 90 | 20.74 | 12.35 |

Summarizing the results of the animal tests it can be stated that applying the pharmaceutical products according to the invention for curing tumorous diseases a recovery rate of about 50% can be attained in the early stage of the disease and the survival period can be increased by 20–30% in an advanced stage of the disease. These results can be further improved by applying water containing even less deuterium.

The products according to the invention can be applied for therapeutical purposes in forms containing the active ingredient together with inert, physiologically acceptable carriers and/or auxiliaries. The active ingredient can be transformed into compositions for oral administration (e. g. solutions, emulsions, suspensions, etc.), parenteral administration (e.g. injectable solutions) or rectal administration (solutions for rectal infusion). The active ingredient can be applied for external use, too, e.g. in the form of ointments.

The pharmaceutical products according to the invention can be prepared by applying known methods conventionally used in the pharmaceutical industry, that is by mixing the active agent and the inert inorganic or organic carriers and then by processing the mixture into galenics.

Water or ethanol can be preferably used as liquid carrier.

The pharmaceutical products can contain also further auxiliaries conventionally used in the pharmaceutical industry, e.g. wetting agents, sweeteners, fragrances, buffering agents etc.

The medicinal solutions according to the invention can be prepared by applying known methods generally used in the food industry for preparing fruit juices, syrups, soft drinks and beer, that is by admixing the active agent with the basic materials of the soft-drink and beer industry such as fruit juices, juice concentrates, flavouring agents, sweeteners, fragrancies,. essential oils as well as other additives and auxiliary agents conventionally used in the soft-drink and beer industry.

The daily dosage of the pharmaceutical products according to the invention can be varied within wide ranges, depending on several factors, e.g. the activity of the active ingredient, the condition and age of the patient, the type of the tumour, the degree of malignity, etc. In the case of a patient of 70 kg body mass the oral daily dose is 1–2 litres of deuterium-depleted fluid containing deuterium in a concentration range of from 0.1 ppm to 110 ppm.

The D-depleted water can contain e.g. 30–50 g of carbohydrate and other flavouring agents or fragrances in order to make the pharmaceutical products tastier.

In case of injectable solutions the daily dose can be up to 2–6 litres and the deuterium concentration of the water can change between wide intervals (0.1–110 ppm). In general, the deuterium concentration of the water in the patients body should be decreased by at least 0.5 ppm daily in order to assure the desired therapeutical effect. These doses are only of informative character, and the dose to be applied should be always prescribed by the medical attendant.

The main advantages of the product and process according to the invention are as follows:
a) The process gives a chance for intervening directly into the regulation mechanism of cell-proliferation in a natural way.
b) Tumorous diseases can be prevented and cured by using the pharmaceutical products according to the invention.
c) The components of the product have no toxical side effects.
d) No wastes harmful for the environment are produced in the manufacturing process.
e) The process can be carried out in a technologically simple way.
f) Mutant cells are not generated in the course of the therapeutical treatment since the active ingredient is not mutagenic. (Most of the cytostatics applied so far have a strong mutagenic character, therefore frequently inducing novel tumours.)
g) The application of the pharmaceutical products according to the invention results in recovering and not in delaying the development of the disease.

The product and process according to the invention are illustrated in more detail in the following examples, without limiting the scope claimed.

EXAMPLE 1

Production of D-depleted water by electrolysis

An aqueous 15–20 w/v % KOH solution is electrolyzed by direct current at a potential of 2–5 V with a cathode and an anode separated from each other. The hydrogen evolving on the cathode and containing deuterium in a decreased concentration is burnt and the steam being formed is condensed and separately collected. The so-obtained water has a deuterium content of 30–40 ppm which is decreased to 6–20 ppm by a further electrolysis.

The so-obtained product can be used for assuring the fluid demand of patients suffering from tumourous diseases and—as starting material—for producing compounds of decreased deuterium content.

The end-product of the process is distilled water, therefore it is preferable to add essential salts before using it for human consumption. The end-product can be advantageously supplemented with a salt mixture containing 1000 mg of sodium, 200 mg of potassium, 160 mg of calcium, 88 mg of magnesium, 650 mg of phosphorous and 600 mg of chlorine, calculated to 1 litre.

EXAMPLE 2

Production of D-depleted water by distillation

The water is distilled in a fractionating column of 30–50 plates under a pressure of 50–60 millibar and at a temperature of 45° to 50° C. The reflux value is maintained between 12 and 13 in the course of the distillation. To keep the D concenration at a low level a tenfold dilution at the bottom is applied during the distillation. Applying these parameters, the deuterium concentration of the head-products is 20–30 ppm. The deuterium content of the water can be decreased to 1–10 ppm by further increasing the plate number and/or by repeating the distillation process.

The end-product of the process is distilled water, therefore it is suitable to add essential salts before using it for human consumption. The salt mixture of Example 1 can be advantageously applied for this purpose.

EXAMPLE 3

Production of D-depleted physiological salt solution 8.5 g of NaCl were added to 1 litre of distilled water prepared according to Example 1 or 2. The physiological salt solution is usually applied as an infusion solution after carrying out the usual sterilization process. Applying this product form the daily dose can be increased to 2–6 litres in serious cases.

EXAMPLE 4

Production of D-depleted fruit juices

Distilled water prepared according to Example 1 or 2 and containing 20–30 ppm of deuterium is mixed with water and fruit juice concentrate as follows:
a) 0.8 part by volume of water containing 20–30 ppm of deuterium+0.2 part by volume of fruit juice concentrate (the final concentration of deuterium is about 45–50 ppm);
b) 0.5 part by volume of water containing 20–30 ppm of deuterium+0.2 part by volume of fruit concentrate+0.3 part by volume of normal water (the final concentration of the deuterium is about 85–90 ppm);
c) 0.3 part by volume of water containing 20–30 ppm of deuterium+0.2 part by volume of fruit juice concentrate+ 0.5 part by volume of normal water (the final concentration of the deuterium is of about 105–110 ppm).

Starting from water containing deuterium in a lower concentration, fruit juices containing even lower deuterium concentration can be prepared.

EXAMPLE 5

Production of D-depleted soft drinks with carbonic acid content

Distilled water prepared according to the Example 1 or 2 and containing 20–30 ppm of deuterium is mixed with soft drink concentrate containing 50 g/l of sugar, 5% by volume of orange juice, 6 g/l of carbonic acid, 1 g/l of citric acid, 500 mg/l of ascorbic acid and 500 mg/l of natural flavouring agents, as follows:

a) 0.8 part by volume of water containing 20–30 ppm of deuterium+0.2 part by volume of soft drink concentrate (the final concentration of the deuterium is about 45–50 ppm);
b) 0.5 part by volume of water containing 20–30 ppm of deuterium+0.3 part by volume of normal water+0.2 part by volume of soft drink concentrate (the final concentration of the deuterium is about 85–90 ppm);
c) 0.3 part by volume of water containing 20–30 ppm of deuterium+0.5 part by volume of normal water+0.2 part by volume of soft drink concentrate (the final concentration of the deuterium is about 105–110 ppm).

Starting from water containing deuterium in a lower concentration, soft drinks containing deuterium in a lower concentration can also be prepared.

EXAMPLE 6

Production of beer having decreased deuterium content

Barley is first soaked in water having 0.1 to 110 ppm deuterium content for producing malt, then germinated at a temperature of 5°–15° C. in a sheet having a thickness of 5–15 cm and under good aeration conditions.

The germinated barley is dehydrated at a temperature between 56° C. and 75° C., separated from the rests of germ roots, and then ground. The ground malt is mixed with a suitable amount of water having a deuterium content of 0.1–110 ppm. The mixture is heated at a temperature between. 50° C. and 75° C., then filtered and brewed with hop. The hopped beer is filtered, cooled and then inoculated with prepropagated Saccharomyces cerevisiae. The period of the primary fermentation process at 5°–6° C. lasts 10–14 days. The secondary fermentation process is carried out in sealed drums at 0° C. for some weeks, then the so-prepared beer is filtered, bottled and pasteurized.

The deuterium content of the beer prepared according to this Example depends on the deuterium content of the applied water which influences the deuterium content of the ethanol and other components, too.

EXAMPLE 7

Production of a hydrating ointment of decreased deuterium content

The hydrating ointment is produced in a conventional way by using D-depleted water. The composition of a generally usable hydrating ointment related to 1000 g of the product is as follows:

| | |
|---|---|
| Unguentum hydrosum | 550 g |
| Unguentum stearini | 150 g |
| Aqua destillata containing 30–40 ppm deuterium | 300 g |

I claim:

1. A pharmaceutical composition for treating a tumorous disease, comprising a pharmaceutically acceptable aqueous solution having a deuterium concentration of from 0.1 to 110 ppm as active agent.

2. The pharmaceutical composition of claim 1 wherein said pharmaceutically acceptable aqueous solution is a physiological salt solution.

3. The pharmaceutical composition of claim 1 wherein said pharmaceutically acceptable aqueous solution is selected from the group consisting of fruit juice, soft drink, and beer.

4. A process for preparing the pharmaceutical composition of claim 1, comprising the steps of:

producing by at least one of electrolysis and distillation water having a deuterium concentration less than the concentration of deuterium in natural water, and transforming said water to one of a pharmaceutical product and a medicinal solution.

5. The process of claim 4, wherein:

said pharmaceutical product is a physiological salt solution, and said pharmaceutical product has a deuterium content of 0.1 to 110 ppm.

6. The process of claim 4, wherein:

said medicinal solution is selected from the group consisting of fruit juice, soft drink and beer, and said medicinal solution has a deuterium content of 0.1 to 110 ppm.

7. The process of claim 4, further comprising the step of formulating said pharmaceutical composition into a form selected from the group consisting of an injectable solution, an infusion solution, a syrup, a juice, and a hydrating ointment.

8. A method of treating a tumorous disease in an organism comprising the step of administering to said organism an effective amount of the composition of claim 1.

9. The method of claim 8 wherein said tumorous disease has a classification selected from the group consisting of a breast cancer, a prostate cancer, a colon cancer, a liver cancer, an ovarian cancer, a sarcoma, a brain cancer, a stomach cancer, a uterogenital cancer, a kidney cancer, a lung cancer, a rectal cancer, a skin cancer, a myeloid leukemia, a leukocytic leukemia, a monocytic leukemia, an aluekothemic leukemia, a myeloma, a lymphoma, a bone cancer, a neuroma, a myoma, an endothelialoma, an epithelioma, a carcinoma, and a melanoma.

10. A method for treating a neoplastic disease comprising:

depleting a deuterium content of water in a material to produce a treatment material having a deuterium concentration substantially below a naturally occurring deuterium level in said material; and administering said treatment material to a patient in a sufficient quantity to reduce a deuterium concentration in said patient to a pharmaceutically effective level below said naturally occurring deuterium level, whereby said neoplastic disease is treated.

11. A method for treating neoplastic disease comprising the steps of:

manufacturing a composition having a water content deuterium concentration of less than a normal physiologic concentration; and administering said composition to a patient, said step of administering including administering a sufficient quantity of said composition whereby a general deuterium concentration in said patient drops to a level below said normal physiologic concentration.

12. A method of treating a tumorous disease comprising the step of applying at least one product having a water content deuterium concentration less than a deuterium content of natural waters to a patient.

13. The method of claim 12 wherein said step of applying is at least one selected from the group consisting of injecting, infusing, feeding, drinking, and topically applying.

14. The method of claim 12 wherein said deuterium concentration less than a deuterium content of natural waters is a concentration in a range of about 0.1 to about 110 ppm.

15. The method of claim 12 wherein said at least one product is one of a water and an aqueous solution.

16. The method of claim 15 wherein said aqueous solution is selected from the group consisting of a physiological salt solution, a reconstituted fruit juice, a soft drink, and a beer.

17. The method of claim 12 wherein said product is a formulation selected from the group consisting of an injectable solution, an infusion solution, a syrup, a juice, and a hydrating ointment.

18. The method of claim 12 wherein each said at least one product having a deuterium concentration less than a deuterium content of natural waters results from a production process where a deuterium depleted water is substituted for a water having a deuterium concentration equal to a deuterium content of natural waters.

19. The method of claim 15 wherein said aqueous solution results from a production process where a deuterium depleted water is substituted for a water having a deuterium concentration equal to a deuterium content of natural waters.

20. The method of claim 15 wherein said water is produced by at least one of electrolysis and distillation.

21. The method of claim 18 wherein said deuterium depleted water is produced by at least one of electrolysis and distillation.

22. The method of claim 19 wherein said deuterium depleted water is produced by at least one of electrolysis and distillation.

23. A method for decreasing a deuterium level in an organism comprising the step of applying a product having a water content deuterium concentration in an amount less than a deuterium content of natural water.

24. The method of claim 23 wherein said step of applying is selected from the group consisting of injecting, infusing, feeding, drinking, and topically applying.

25. The method of claim 23 wherein said deuterium concentration less than a deuterium content of natural waters is a concentration in a range of about 0.1 to about 110 ppm.

26. The method of claim 23 wherein said at least one product is at least one of water or an aqueous solution.

27. The method of claim 26 wherein said aqueous solution is selected from the group consisting of a physiological salt solution, a fruit syrup, a soft drink, and a beer.

28. The method of claim 23 wherein said product is in a form selected from the group consisting of an injectable solution, an infusion solution, a syrup, a juice, and a hydrating ointment.

29. The method of claim 23 wherein said product results from a production process where a deuterium depleted water is substituted for a water having a deuterium concentration equal to a deuterium content of natural waters.

30. The method of claim 26 wherein said aqueous solution results from a production process where a deuterium depleted water is substituted for a water having a deuterium concentration equal to a deuterium content of natural waters.

31. The method of claim 26 wherein said water is produced by at least one of electrolysis and distillation.

32. The method of claim 29 wherein said deuterium depleted water is produced by at least one of electrolysis and distillation.

33. The method of claim 30 wherein said deuterium depleted water is produced by at least one of electrolysis and distillation.

34. A method of treating a tumorous disease in an organism, comprising the step of administering to said organism an effective amount of the composition of claim 1, wherein said tumorous disease has a classification selected from the group consisting of a breast tumor, a lung tumor, a rectal tumor, a colon tumor, and a prostate tumor.

* * * * *